United States Patent [19]

Fraering, Jr. et al.

[11] Patent Number: 5,712,677
[45] Date of Patent: Jan. 27, 1998

[54] APPARATUS FOR VIDEO INSPECTION OF THE INTERIOR SURFACE OF TUBULAR GOODS

[76] Inventors: Camille M. Fraering, Jr.; Phillip G. Fraering; George C. Fraering, all of 415 Mecca Dr., Lafayette, La. 70508

[21] Appl. No.: 422,592

[22] Filed: Apr. 14, 1995

[51] Int. Cl.$^6$ .................. H04N 7/18; H04N 9/47
[52] U.S. Cl. .................. 348/84; 348/85
[58] Field of Search .................. 348/84, 85, 87, 348/91, 92, 125–131; 356/241; 600/109; 385/36, 119; 250/256

[56] References Cited

U.S. PATENT DOCUMENTS

| | | | |
|---|---|---|---|
| 2,632,801 | 3/1953 | Donaldson | 348/85 |
| 2,849,530 | 8/1958 | Fleet | 348/85 |
| 3,279,085 | 10/1966 | Reinhart | 348/85 |
| 3,586,872 | 6/1971 | Tien | 307/88.3 |
| 3,837,827 | 9/1974 | Carruthers et al. | 65/30 |
| 3,855,547 | 12/1974 | Kirk | 331/94.5 |
| 4,027,946 | 6/1977 | Tsai | 350/96 |
| 4,152,045 | 5/1979 | Hammer | 350/96.19 |
| 4,255,762 | 3/1981 | Takeyasu et al. | 348/84 |
| 4,532,545 | 7/1985 | Hanson | 348/83 |
| 4,823,187 | 4/1989 | Toyama et al. | 348/263 |
| 4,899,921 | 2/1990 | Bendat et al. | 348/87 |
| 4,914,289 | 4/1990 | Nguyen et al. | 250/223 |
| 5,008,043 | 4/1991 | Robello et al. | 252/582 |
| 5,140,319 | 8/1992 | Riordan | 348/85 |
| 5,402,165 | 3/1995 | Linville et al. | 348/85 |
| 5,432,600 | 7/1995 | Grollimund et al. | 356/237 |
| 5,434,669 | 7/1995 | Tabata et al. | 356/345 |
| 5,444,567 | 8/1995 | Kataoka | 359/319 |

*Primary Examiner*—Tommy P. Chin
*Assistant Examiner*—Y. Lee
*Attorney, Agent, or Firm*—The Onebane Law Firm

[57] ABSTRACT

The apparatus for video inspection of the interior surface of tubular goods, includes: an elongated mounting plate having a first and a second end; a first compartment at the first end of the mounting plate which has a light transmissive window facing the second end of the mounting plate; a second compartment at the second end of the mounting plate which has a light diffusing window facing the first end of the mounting plate; a video camera having a wide angle lens in the first compartment; a light source in said second compartment; a first prism disposed in front of said lens; and, external means for monitoring and recording camera output.

The wide angle lens in combination with the first prism provides for a dual field of view, part of which is transmitted through the first prism for viewing a small circumferential area opposite the inclined side of the first prism, and, part of which constitutes a peripheral view of nearly the entire circumference, "C", of the tubular received directly by the lens. Light reflecting from nearly the entire circumference, "C", of the tubular provides means for general inspection of large areas of the tubular for suspected defects, "D". Light transmitted through the prism provides a means for close inspection of suspected defects, "D", and movement of the prism closer to the lens provides for greater magnification thereof. Light from the light source may be diverted through a second prism to provide greater illumination and shadowing of suspected defects, "D", in the magnified area.

6 Claims, 3 Drawing Sheets

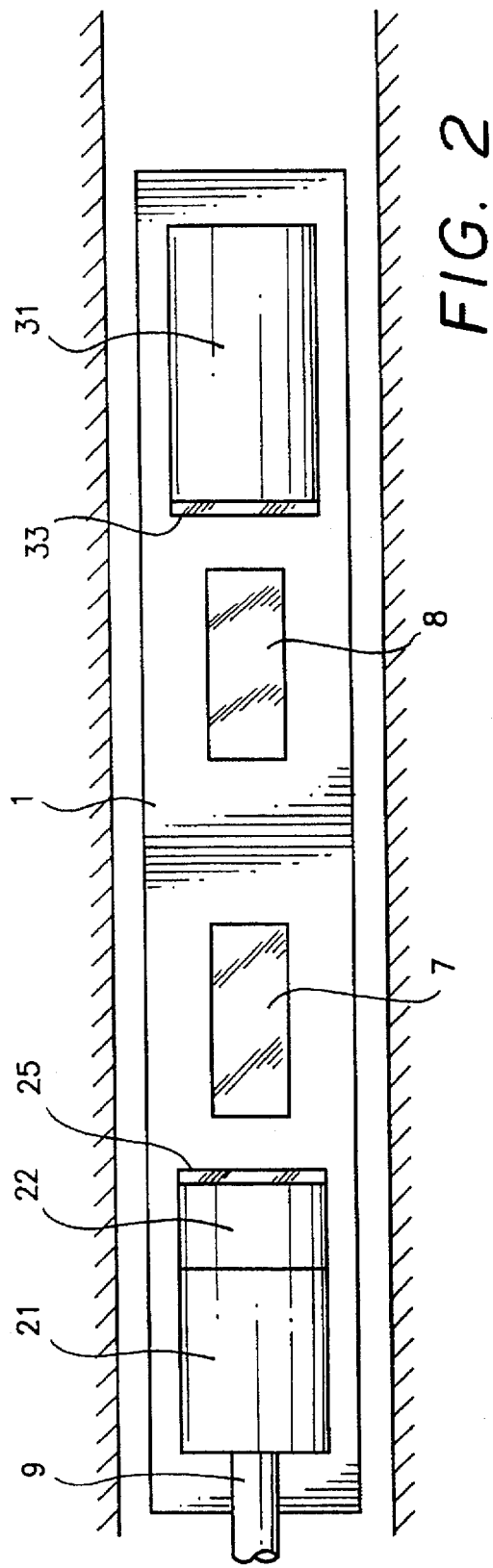
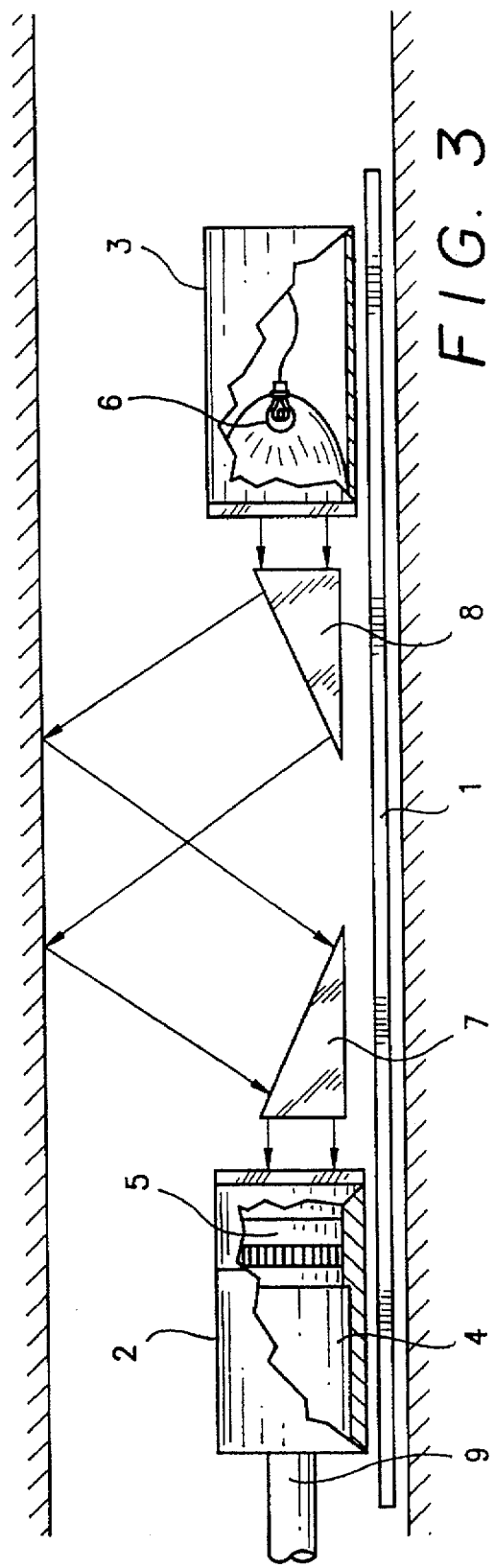

5,712,677

APPARATUS FOR VIDEO INSPECTION OF THE INTERIOR SURFACE OF TUBULAR GOODS

BACKGROUND OF THE INVENTION

A. Field of the Invention

The invention herein disclosed and claimed relates to apparatus for inspecting the inner surface of tubular goods for possible defects. More particularly the invention herein relates to apparatus for generating, displaying and recording of video images of the inner surface of a tubular being inspected. With somewhat greater particularity the invention herein relates to apparatus having a dual field of view, whereby possible defects can be inspected both at acute and obtuse angles, under variable lighting conditions, and with increased magnification.

B. Description of Related Art

In the field of petroleum exploration, development and production literally miles of tubular goods are assembled, disassembled, reassembled, subjected to repeated handling and subjected to extreme downhole conditions. Suffice to say that the integrity of the tubular goods used in said processes is important, and the unexpected failure of a tubular is at best a nuisance, at worst can present life threatening risks.

As even small defects in a tubular can and often do worsen under the effect of corrosion, high pressure, tensile and compressive forces, erosion due to high velocity flows, etc., a need has arisen for careful inspection of tubulars to be used in such applications. Accordingly various techniques are employed in the inspection of tubular goods, including various electro-magnetic techniques, techniques employing gamma rays, ultra-sound, etc. There has even been some attempt to visually inspect the interior of tubulars using manual borescopes and mirrors, but this has been generally found unsatisfactory due to the time and expense involved.

An object of the invention disclosed herein is to provide a video apparatus for, illuminating, displaying, inspecting and/or recording the interior surface of tubular goods. Another object of the invention disclosed herein is to provide an apparatus having a dual field of view, one field of which is comprised of a wide angle view of an axial section of nearly the entire circumference of the tubular for general viewing and the other field of view being a narrow angle view of a small section of the tubular, for enhanced inspection.

SUMMARY OF THE INVENTION

The invention disclosed and claimed herein is characterized by an insertable probe having a camera and a light source facing each other from opposite ends of a mounting plate. A wide angled lens disposed on the camera provides for good peripheral viewing of an axial band of nearly the entire circumference of the tubular. A Littrow prism disposed in front of the camera lens precludes light emanating directly from the light source from entering the camera and diverts the image of a small portion of the tubular interior which is opposite the hypotenuse of the prism into the camera. Movement of the prism closer to the camera increases the magnification of that portion of the tubular viewed through the prism. A second prism, disposed in front of the light source, may be used to increase lighting intensity and shadowing in the area being viewed by the Littrow prism.

A flexible hose serves as a conduit for power and video wiring, and, is used to control positioning of the probe inside of a tubular during inspection of the tubular. Pressure may be increased or decreased in said hose to provide same with more or less stiffness and longitudinal stiffeners may be added to the external of the hose if desired.

Operation of the apparatus is accomplished by inserting the probe into the interior of a tubular to be inspected and causing same to traverse the entire axial length of the tubular. As the probe travels the length of the tubular, successive axial bands of nearly the entire inner circumference of the tubular become illuminated and are viewed by the camera. Video-output of the camera is fed from the probe, through the flexible hosing and into externally disposed CRT, other video display and/or videotape recorder. If during said general inspection the operator desires to inspect a specific area of the tubular surface in greater detail, the probe is positioned inside of the tubular so that the area for enhanced inspection is opposite the hypotenuse of the Littrow prism. Movement of the Littrow prism towards the lens of the camera increases the size of the image. The second prism may be moved closer to the light source to divert additional light from the light source to the area opposite the hypotenuse of the Littrow prism or the distance between the second prism and the Littrow prism may be varied to produce increased shadowing in that area.

BRIEF DESCRIPTION OF THE DRAWINGS

FIG. 2 is an overhead plan view of the apparatus of the present invention.

FIG. 3 is a side plan view of the apparatus of the present invention, showing the interaction of the two prisms of the present invention.

DESCRIPTION OF THE PREFERRED EMBODIMENT

Figure 1:
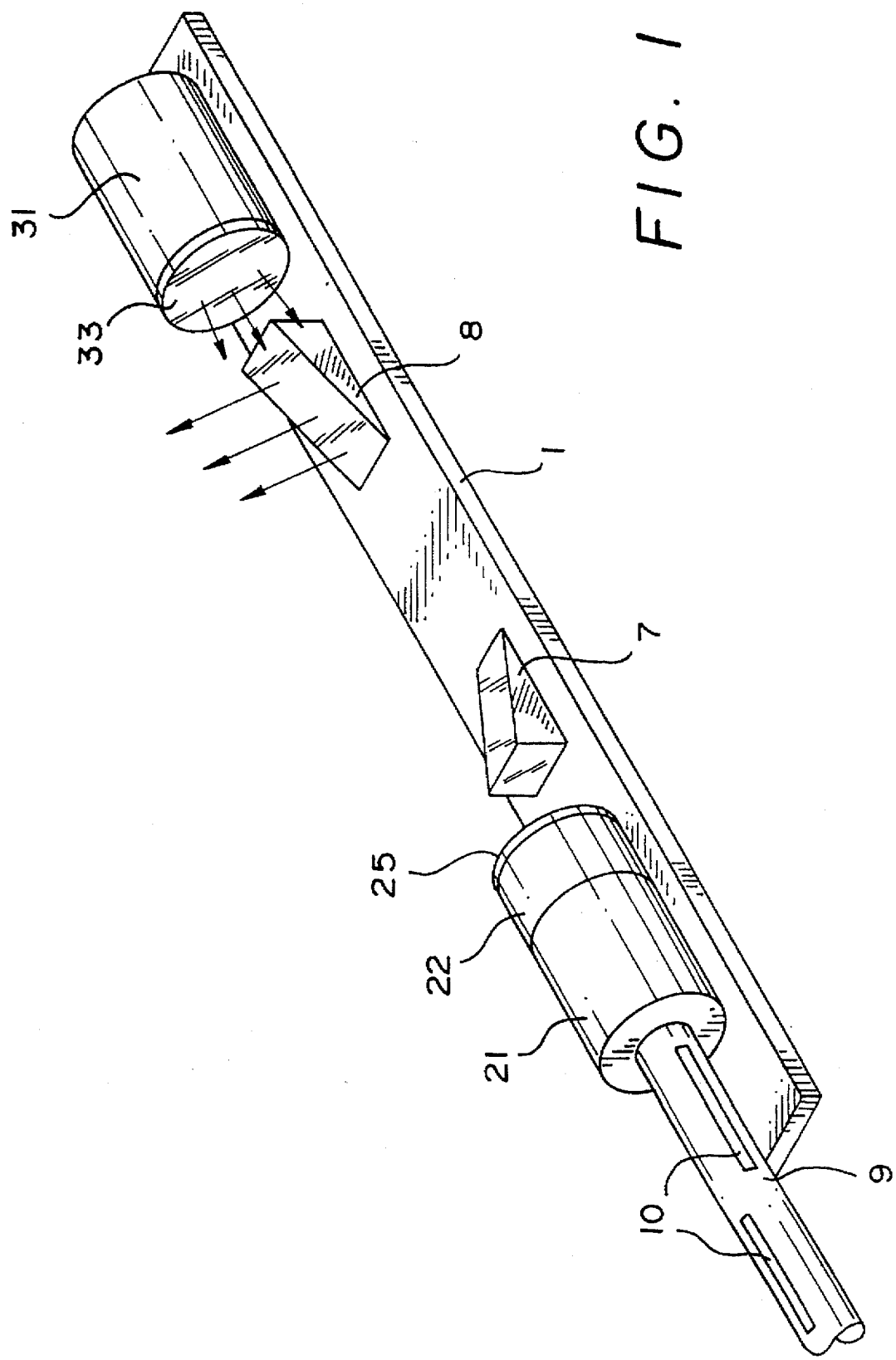
FIG. 1 is an oblique perspective view of the apparatus of the present invention.
Figure 4:
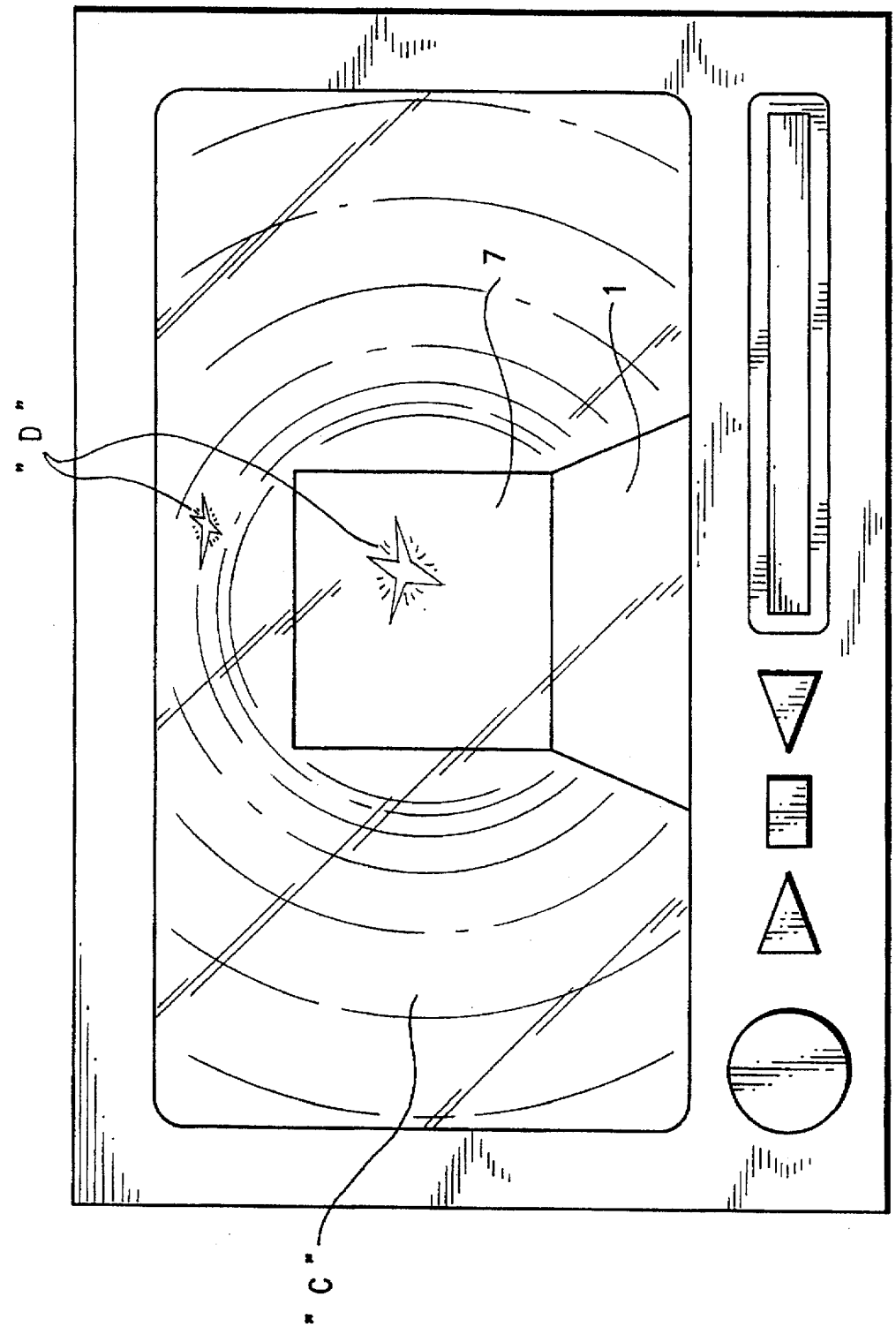
FIG. 4 show an exemplary type of display obtained with the apparatus of the present invention.

The preferred embodiment of the invention includes: elongated mounting plate having a first end and a second end, 1; a first compartment, 2, near the first end of said mounting plate having a light transmissive window, 25, facing the second end; a second compartment, 3, near the second end having a light diffusing window, 33, facing the first end; a video camera, 4, having a wide angle lens, 5, disposed in the first compartment; an electric light source, 6, disposed in the second compartment; a Littrow prism disposed an adjustable distance in front of the camera window; a second prism, 8, disposed an adjustable distance in front of the diffusing window, 33, of light source, 6; flexible hose means, 9, attached to said first compartment, 2; hose stiffener means, 10, and means for displaying and recording video output of the camera.

Beginning with elongated mounting plate, 1, in the preferred embodiment, is of elongated, arcuate configuration, wherein the radius of the arc is the same or only slightly larger than the radius of the longest component to be mounted on the mounting plate, 1. Maintenance of this relationship between the size of the largest component to be mounted and the curvature of the mounting plate, 1, allows for maximum recessing of the components with minimal contribution of the plate to cross-sectional area of the insertable probe.

Next, is compartment, 2. Compartment, 2, includes a generally cylindrical camera housing, 21, a generally cylindrical lens housing, 22, plug, 23, hose fitting, 24, window, 25. When assembled compartment, 2, provides a sealed unit protecting camera, 4, and lens, 5, from moisture, dirt and other potentially injurious substances. Flexible hose, 9, attached to hose fitting, 24, of plug, 23, provides a conduit for the passage of electrical wiring into and from compartment, 2, and provides a means for positioning of the probe once it is inserted into a tubular. Ability to position the probe inside a tubular may be enhanced by stiffening the flexible hose, by increasing pneumatic pressure therein, or by attaching external stiffener bars, 10. Additional protection of the camera and lens from fluid, or even small particulate intrusion into compartment, 2, is enhanced by maintaining a "positive pressure" in compartment, 2, with respect to the pressure outside of compartment, 2, and may be accomplished by introduction of pressurized gas (such as air, nitrogen, etc.) into compartment, 2, through hose, 9, and hose fitting, 24.

Compartment, 2, is generally positioned near the first end of elongated mounting plate, 1, with window, 25, of compartment, 2, facing the second end of said elongated mounting plate. Camera, 4, and lens, 5, are disposed within compartment, 2, with the front of lens, 5, disposed near window, 25, as lens, 5, is a wide angle lens (generally having a focal length between 3.5 and 12 millimeters and the farther it is recessed in compartment, 2, the more likely it is that part of the interior compartment itself will come into the camera's field of view and obstruct at least part of the view of the tubular to be inspected). Window, 25, is made of high grade optical quality glass so as to minimize distortion or loss of image quality when the inside of a tubular is viewed through window, 25.

Continuing further with the preferred embodiment is compartment, 3. Compartment, 3, includes generally cylindrical housing, 31, plug, 32, and light diffusing window, 33. Compartment, 3, provides a sealed unit for protection of an electric light source enclosed therein from the deleterious effects of moisture, dirt and chemicals.

Compartment, 3, is disposed at the opposite end (second end) of mounting plate, 1, from compartment, 2; and light diffusing window, 33, of compartment, 3, is facing window, 25, of compartment, 2. Window, 33, is made of optical diffusing glass, sometimes referred to as "opal glass", which evenly diffuses light throughout the interior of the section of the tubular being viewed (generally, that section between window, 25, and light diffusing window, 33).

Inside of compartment 3, is light source 6 which includes an electric bulb and a reflector directing light therefrom onto light diffusing window, 33. Applicant has found it desirable to provide a means for externally controlling the intensity of light, 6, thus provides power to same from external power supply controlled by rheostat. Power wiring for light, 6, is fed through hose, 9, and hose fitting, 24, into compartment, 2, and then from compartment, 2, to compartment, 3, by jumper wiring.

Continuing further with a detailed description of the preferred embodiment of the invention is next illustrated prism, 7. The preferred angles of prism, 7, are substantially 90 degrees, 60 degrees and 30 degrees and it leg opposite the 60 degree angle is coated with a substantially reflective coating. This type of prism diverts images by a 60 degree angle without inverting or reverting the image and is commonly referred to as a "Littrow prism". Prism, 7, is disposed between window, 25, and light diffusing window, 33, with the side opposite the 30 degree angle facing window, 25, and the side opposite the 60 degree angle disposed parallel to mounting plate, 1. So disposed prism, 7, prevents light emanating directly from the light source from entering the camera and prism, 7, and also diverts the view of a least a portion of the camera by 60 degrees without inverting or reverting the image viewed.

By appropriate sizing of prism, 7, and selection of its distance away from window, 25, the camera has a dual field of view. The image viewed peripherally to the prism, 7, constitutes a wide angle view of an axial band (that band generally between the light source, 6, and the camera lens, 5) of nearly the entire circumference, "C", of the tubular interior. The image viewed within the borders of the prism, 7, is actually an image of a small section of the tubular interior which is opposite the hypothenuse of the prism, 7. Movement of the prism, 7, closer to window, 25, enlarges the image, effectively magnifying it. Thus the prism, 7, provides a means for close inspection of possible defects, "D".

Optionally the preferred embodiment may also include a second prism, 8, disposed between prism, 7, and light diffusing window, 33. The object of prism, 8, is to intercept part of the light emanating from window, 33, and redirect it to the zone on the inside of the tubular which is opposite to the hypotenuse of prism, 7. Stronger lighting in this zone increases shadowing resulting from surface defects, "D", which frequently makes the defects, "D", easier to visualize. As the optimum distance between prism, 8, light diffusing window, 33, prism, 7, and window, 25, varies for different size tubular goods, each of these components is adjustably disposed along the longitude of mounting plate, 1. In the preferred embodiment inventors use a conventional screw in a slotted channel to position compartments, 2, and, 3, and hook tape (such as Velcro) for prisms, 7, and, 8), but nearly any equivalent means of adjustably positioning objects on a surface would work as well.

Typically the apparatus is operated from an external console containing power supply for the camera, 4, power supply for the light source, 6, a CRT or other video display equipment and a video cassette recorder. Power and video signal data is transmitted to and from the apparatus through flexible hose, 9, which connects to hose fitting, 24. Inspection of a tubular is conducted by inserting the apparatus into one end of a tubular and causing same to slowly traverse the axial length of the tubing while camera output is monitored and, if desired, recorded. Generally during axial movement of the apparatus through the tubing the operator will focus his attention on that portion of the display which is peripheral to the Littrow prism, 7, appearing in the center of the display, as the peripheral view covers a much larger area (nearly the entire circumference, "C", of the tubular inner diameter). If however a suspicious appearing area is detected by peripheral viewing then a more detailed inspection of that suspicious area may be conducted by viewing that area through the Littrow prism, 7. In order to move the suspicious area into the view of the Littrow prism, 7, the apparatus may have to be rotated and/or repositioned axially within the tubular. Hose, 9, possibly pressurized for increased stiffness and/or with hose stiffeners, 10, placed thereon may be used as a semi-rigid handle to accomplish said positioning or repositioning of the apparatus within the tubular.

While the invention has been by way of currently preferred embodiments, numerous alternatives within the spirit and scope of the invention will be apparent to those skilled in the art and the invention is intended to be limited only by the claims.

We claim:

1. An apparatus for inspection of the interior surface of tubular goods, comprising:

a) an elongated mounting plate having an upper surface and a longitudinal axis which is substantially contiguous with said upper surface;

b) a video camera disposed on said elongated mounting plate, said video camera having a lens, said lens having an axis substantially parallel to the longitudinal axis of said elongated mounting plate and substantially contiguous with a plane substantially coincident with the longitudinal axis of the elongated mounting plate and disposed substantially perpendicularity to the surface of said elongated mounting plate;

c) a light source disposed on said elongated mounting plate at a position spaced apart from said video camera, said light source having a longitudinal axis disposed substantially contiguous with the axis of the lens of the video camera, having a light diffusing window disposed substantially perpendicularly to said axis of said lens of said vide camera and substantially facing the lens of said video camera, forming an illuminated viewing area between said window of said light source and said lens of said video camera;

d) a first and a second prism disposed between the lens of said video camera and the window of said light source, wherein said first prism is disposed between the lens of said camera and said second prism and is comprised of first, second and third planar surfaces, said first planar surface facing the lens of the video camera and disposed perpendicular to the axis of the lens of said video camera, said second planar surface having an axis disposed along a line substantially parallel to the axis of the lens of said video camera and said third planar surface intersecting a plane parallel to the upper surface of the elongated mounting plate at an oblique angle, said first prism reflecting light from a portion of the interior surface of tubular good being inspected into the lens of the video camera; and, e) said second prism is disposed between said first prism and the window of said light source and is comprised of first, second and third planar surfaces, said first planar surface facing the window of the light source and disposed perpendicular to the longitudinal axis of the light source, said second planar surface having an axis disposed along a line substantially parallel to the longitudinal axis of the light source and said third planar surface intersecting a plane parallel to the upper surface of the elongated mounting plate at an oblique angle, said second prism directing at least a portion of light from the light source to said portion of the interior surface of tubular good from which light is being reflected into the lens of the video camera.

2. The apparatus of claim 1 wherein the first prism is a Littrow prism.

3. The apparatus of claim 1 wherein the video camera is enclosed in a sealed compartment having a light transmissive window.

4. The apparatus of claim 1 wherein the light source is enclosed in a sealed compartment having a light diffusing window.

5. The apparatus of claim 1 wherein the video camera, light source, first prism and second prism are disposed along a common axis.

6. The apparatus of claim 1 wherein the distance of the second prism from the first prism is selectively variable.

* * * * *